(12) United States Patent
Zichun et al.

(10) Patent No.: US 11,324,796 B2
(45) Date of Patent: May 10, 2022

(54) METHOD FOR REGULATING LIPOLYSIS AND FATTY ACID OXIDATIVE METABOLISM

(71) Applicant: Nanjing University, Najing (CN)

(72) Inventors: Hua Zichun, Nanjing (CN); Zhuang Hongqin, Nanjing (CN)

(73) Assignee: Nanjing University, Nanjing (CN)

( * ) Notice: Subject to any disclaimer, the term of this patent is extended or adjusted under 35 U.S.C. 154(b) by 379 days.

(21) Appl. No.: 16/311,221

(22) PCT Filed: Nov. 24, 2016

(86) PCT No.: PCT/CN2016/107038
§ 371 (c)(1),
(2) Date: Dec. 19, 2018

(87) PCT Pub. No.: WO2017/219601
PCT Pub. Date: Dec. 28, 2017

(65) Prior Publication Data
US 2021/0069283 A1    Mar. 11, 2021

(30) Foreign Application Priority Data

Jun. 21, 2016 (CN) .......................... 201610453256.7

(51) Int. Cl.
| | | |
|---|---|---|
| *A61K 38/00* | (2006.01) | |
| *A61P 3/04* | (2006.01) | |
| *A61K 31/20* | (2006.01) | |
| *A61K 31/7088* | (2006.01) | |
| *A61K 31/715* | (2006.01) | |

(52) U.S. Cl.
CPC .............. *A61K 38/00* (2013.01); *A61K 31/20* (2013.01); *A61K 31/7088* (2013.01); *A61K 31/715* (2013.01); *A61P 3/04* (2018.01)

(58) Field of Classification Search
CPC .. A61K 31/20; A61K 31/7088; A61K 31/715; A61K 38/00; A61K 45/00; A61K 48/00; A61P 3/00; A61P 3/04; A61P 3/06; G01N 33/68
See application file for complete search history.

(56) References Cited

U.S. PATENT DOCUMENTS

2021/0147842 A1* 5/2021 Yuan .................. C12N 15/1137

FOREIGN PATENT DOCUMENTS

CN        103239737        8/2013

OTHER PUBLICATIONS

Alappat et al. Cell Cycle Effects by C-FADD Depend on Its C-terminal Phosphorylation Site. The Journal of Biological Chemistry, Vo. 278, No. 43, pp. 41585-41588. (Year: 2003).*
Hua et al. A Function of Fas-Associated Death Domain Protein in Cell Cycle Progression Localized to a Single Amino Acid at Its C-Terminal Region. Immunity, vol. 18, pp. 513-521. (Year: 2003).*
Zhuang et al. FADD is a key regulator of lipid metabolism. EMBO Mol Med, 2016, vol. 8, pp. 895-918. (Year: 2016).*
Yao et al. Role of Fas-Associated Death Domain-containing Protein (FADD) Phosphorylation in Regulating Glucose Homeostasis: fromProteomic Discovery to Physiological Validation. Molecular and Cellular Proteomics, 12.10, pp. 2689-2700. (Year: 2013).*
Zhuang,Hongqin etc., Comparative Proteomics analysis reveals roles for FADD in the regulation of energy metabolism and proteolysis pathway in mouse embryonic fibroblast, Proteomics, Aug. 31, 2013, No. 16, vol. 13, pp. 2398-2413.
Dan Zhao, FADD Research Progress, J. of International Immunology, May 5, 2006, No. 3, vol. 29, pp. 152-156.

* cited by examiner

*Primary Examiner* — Marcela M Cordero Garcia

(57) ABSTRACT

Provided are a method for promoting the lipolysis and fatty acid oxidative metabolism in mammals or cells derived from mammals, a method for downregulating the fat content and the weight of a mammalian body, as well as a method for increasing the intracellular cAMP concentration, increasing the phosphorylation degree and the activity of the hormone-sensitive esterase HSL, enhancing the transcription activity of PPAR alpha and increasing the activities of enzymes involved in a fatty acid beta oxidation process. By simulating the expression of a protein corresponding to a gene responsible for the phosphorylation of the Fas-associated death domain protein, or treating and acting on mammals or cells derived from mammals with a material that can increase the phosphorylation degree of the Fas-associated death domain protein, said methods increases the phosphorylation of the Fas-associated death domain protein.

6 Claims, 11 Drawing Sheets
Specification includes a Sequence Listing.

white adipose tissue white adipose tissue

METHOD FOR REGULATING LIPOLYSIS AND FATTY ACID OXIDATIVE METABOLISM

CROSS-REFERENCE TO RELATED APPLICATIONS

This application is a National Stage of International Application No. PCT/CN2016/107038, filed on Nov. 24,2016, and which claims the benefit of the filing date of Chinese Patent Application No. 201610453256.7, filed on Jun. 21, 2016. The entire contents of each of which are hereby incorporated herein by reference in their entireties. The invention relates to the field of biopharmaceutics, and in particular, relates to a method for regulating lipolysis and fatty acid oxidation metabolism and the use thereof.

TECHNICAL FIELD

The invention relates to the field of biopharmaceutics, and in particular, relates to a method for regulating lipolysis and fatty acid oxidation metabolism and the use thereof.

BACKGROUND ART

Triglycerides are the predominant form of energy storage in mammalian cells. When energy intake exceeds energy expenditure, excess energy will be stored in the form of triglycerides in fat cells and tissues containing fat cells and livers, which will eventually lead to cellular energy accumulation and obesity. Animal fat cell lipolysis is a complex process that is regulated by various hormones and physiological signals, and an imbalance of the regulation can lead to obesity and related diseases. The degradation of triglycerides in fat cells is a delicate regulation process, which is closely related to maintaining the dynamic balance of cell or body energy and metabolic health. Decreased lipolytic activity promotes accumulation of triglycerides in adipose tissues. Excessive lipolysis may lead to lipodystrophy syndrome, and a decrease or redistribution of adipose tissue triglycerides results in high concentrations of circulating fatty acids and ectopic storage of triglycerides. The lipolysis of triglycerides is catalyzed by at least three enzymes: adipocyte triglyceride (ATGL) that mainly catalyzes the hydrolysis of the first ester bond of the triglyceride, and the resulting diacylglycerol is catalyzed by hormone sensitive esterase (HSL) to produce monoacylglycerols, and monoacylglycerols are catalyzed by monoacylglycerol esterase (MGL) (Jaworski K et al., 2007, Am J Physiol Gastrointest Liver Physiol 293:1-4). ATGL and HSL are the most important lipolytic enzymes in adipocytes, which together control 95% hydrolysis activity of triglycerides in mouse white adipose tissue (Schweiger M et al., 2006, J Biol Chem 281: 40236-40241). Fatty acids produced by lipolysis can be released into blood, and combined with albumin to form lipoprotein albumin for transporting to other tissues for utilization. The decomposition of fatty acids is carried out in the form of oxidation, and the modes of oxidation include α-oxidation, β-oxidation and ω-oxidation, of which β-oxidation is the primary mode.

HSL is a classical lipolysis rate-limiting enzyme. The substrate includes almost all lipids except phospholipids, including triglycerides, diacylglycerols, monoacylglycerols, cholesterol esters and retinyl esters, and HSL is thought to be lipolysis regulating enzyme. The enzyme hydrolyzes triglyceride to produce monoacylglycerol, which is completely hydrolyzed by its hydrolase. Phosphorylated HSL is its active form and its activation is dependent on the cAMP-PKA pathway. HSL knockout mice do not exhibit obesity and their adipose tissue has triglyceride hydrolytic activity (Fortier M et al., 2004, Am J Physiol Endocrinol Metab 287: 282-288; Haemmerle G et al., 2002, J Biol Chem 277:4806-4815). The hydrolysate diacylglycerol accumulates in white adipose tissue, brown adipose tissue, muscle and testis (Haemmerle G et al., 2002, J Biol Chem 277: 4806-4815). These results indicate that HSL is the rate-limiting enzyme for the hydrolysis of diacylglycerols in adipose tissue and muscle. When the lipolysis reaction occurs, the ATGL-catalyzed reaction is specific to the hydrolysis of the first fatty acid of TG, and produces DG, and the utilization of DG is dependent on the cellular metabolic state (Lass A et al., 2006, Cell Metabolism 3(5): 309-31). Where energy is needed, catecholamines bind to the beta-adrenergic receptor and G-protein mediated signaling activates adenylatecyclase. High levels of cyclic adenosine monophosphate (c-AMP) activate PKA, which further phosphorylates HSL and Perilipin A. Phosphorylated Perilipin A promotes phosphorylation of HSL from cytosolic ectopic to lipid droplet surface by altered conformation. Phosphorylated HSL is adjacent to phosphorylated Perilipin A and binds to TG and DG substrates in fat droplets. DG is further hydrolyzed by HSL to monoacylglycerol (MG) and fatty acid (FA). MG is hydrolyzed to glycerol and FA by monoacylglycerolase, and fatty acids and glycerol leave the fat cells and enter the circulation. Numerous studies have shown that factors such as nutrients and hormones regulate the degradation of fat in adipose tissue (Jaworski K et al., 2007, Am J Physiol Gastrointest Liver Physiol 293: 1-4; Lass A et al., 2006, Cell Metabolism 3 (5): 309-31). In the fed state, insulin reduces cAMP levels by causing HSL dephosphorylation and phosphodiesterase activation, thereby inhibiting lipolysis (Carmen G Y et al., 2006, Cell Signal 18: 401-408; Langin D et al., 2006, Pharmacol Res 53(6): 482-491).

Peroxisome proliferator-activated receptors (PPARs), as a nuclear receptor, regulate the expression of a variety of nuclear genes, and their encoded proteins and other nuclear receptors have similar functional and structural regions. PPARs have been found to have three different subtypes, named PPARα, PPARβ, and PPARγ, respectively. The three subtypes are similar in structure, but their tissue distribution is different. The PPARα subtype is mainly distributed in heart, liver, kidney and skeletal muscle cells with high fatty acid oxidation rate (Issemann I et al., 1990, Nature 347, (6294): 645-650). PPARα plays an important role in regulating fatty acid metabolism and promotes the uptake, transport, activation and β-oxidation of fatty acids. PPARα and its agonists have the effects of eliminating lipid metabolism disorders, improving insulin resistance and reversing cardiac hypertrophy, and have a cardiovascular protective effect. The activated PPARα binds to PPRE and activates the expression of acetyl-CoA synthetase and fatty acid transporter, and activates carnitine acyltransferase-1 (CPT-1) to improve the efficiency of fatty acid uptake, transport and oxidation, and in turn, promotes beta oxidation of fatty acids, increases lipid metabolism, and provides more energy to the body. Mice deficient in the PPARα gene exhibited phenotypes such as obesity and adipocyte enlargement (Costet P et al., 1998, J Biol Chem 273(45): 29577-29585; Knauf C et al., 2006, Endocrinology 147: 4067-4078).

Abnormal cell lipid metabolism is the main pathological factor leading to metabolic syndrome such as obesity and nonalcoholic fatty liver. The prevalence of obesity is growing rapidly worldwide, in both developed and developing countries. Therefore, the key transcription factors or catalytic enzymes in the process of lipid metabolism that can effectively promote the lipolysis process of triglycerides and increase the oxidation rate of fatty acids will be one of the important targets for the treatment of obesity and related diseases, and is the key to treatment.

FADD (Fas-associated death domain protein) is an important adaptor protein in the apoptotic signaling pathway, which mediates the apoptotic signaling pathway induced by Fas and other death receptors. In 1995, two research groups, Dixit and Wallach, used the yeast two-hybrid system and found human and mouse FADD/MORT1 genes almost simultaneously (Chinnaiyan A M et al., 1995, Cell 81(4): 505-512; Boldin M P et al. 1995, J Biol Chem 270 (14): 7795-7798). The human FADD gene is about 3.6 kb and contains two exons (286 bp and 341 bp, respectively) and a 2 kb intron between them. This gene is located on the long arm of chromosome 11 (11q13.3) (Kim P K et al., 1996, J Immunol 157(12): 5461-5466), FADD colocalizes with type 1 diabetes susceptible site (IDDM4) which is located at 11q13 (Eckenrode S et al., 2000, Hum Genet 106(1): 14-18; Nakagawa Y et al., 1998, Am J hum Genet 63(2): 547-556). Therefore, mutations in the FADD gene may affect the development of insulin-dependent diabetes. The human and mouse FADD genes encode a FADD protein consisting of 208 and 205 amino acids, respectively. 68% amino acid residues of the human and mouse FADD proteins are identical, with a degree of homology of up to 80% in the primary structure of the protein. Both human and mouse FADD proteins include three domains: death domain (DD), death effect domain (DED), and C-terminal domain (CTD). The death effect domain DED consists of approximately 76 amino acid residues, and is close to the N-terminus, oligomerizable and recruits DED-containing proteins through hydrophobic interactions to form a death inducing signal complex (DISC). Death receptor-mediated apoptosis signals are transmitted downstream. The death domain DD consists of approximately 70 amino acid residues, and is close to the C-terminus and partially overlaps the CTD domain, and interacts with the DD domain of Fas to receive an apoptotic signal. The C-terminal domain CTD consists of approximately 20 amino acid residues and contains Ser and Thr residues that are susceptible to phosphorylation and may be associated with FADD-mediated non-apoptotic function of cells (Hua Z C et al., 2003, Immunity 18: 513-521).

Mutation of Ser and Thr residues that are susceptible to phosphorylation in proteins to aspartic acid or glutamic acid is a method of studying protein phosphorylation that has been widely recognized and used internationally. For example, Kim Y et al. mutated the serine at position 310 of the WAVE1 protein into aspartic acid to mimic its phosphorylation status in its study (Kim Y et al., 2006, Nature 442 (7104): 814-817); Paroo Z et al. in their study mutated the serine of 142, 152, 283, and 286 of TRBP protein into aspartic acid to mimic its phosphorylation status (Paroo Z et al., 2009, Cell 139: 112-122); Papinski D et al. mutated Atg9 protein serine residues (S802, S831, S948 and S969) into aspartic acid to mimic their phosphorylation status in their study (Papinski D et al., 2014, Mol Cell 53(3): 471-483); Bajorek M et al. in their study, mutated the serine at position 220 of the RSV matrix protein to aspartic acid to mimic its phosphorylation status (Bajorek M et al., 2014, J Virol 88(11): 6380-6393); Pozo-Guisado E et al. in their study replaced the serines of the STIM1 proteins at positions 575, 608 and 621 with glutamate to mimic their phosphorylation (Pozo-Guisado E et al., 2013, J Cell Sci 126 (Pt 14): 3170-3180); Bin L et al., when studying the TnI protein, mutated threonine at position 144 to aspartic acid and glutamic acid to mimic its phosphorylation (Lin B et al., 2014, PLoS One 9(1): e86279). Many experiments have proven that mimicking phosphorylation of serine with aspartic acid or glutamate is reliable whether in charge, in carbon chain length, or functionally. Therefore, it is a routine and feasible method to mutate the FADD protein 191 serine to aspartic acid to study its phosphorylation function.

To date, kinases that have been found to regulate the phosphorylation status of FADD include a 37 kD-sized CKIα protein (Alappat E C et al., 2005, Mol Cell 19:321-332) and a 130 kD-sized FIST-HIPK3 protein (Rochat-Steiner V et al., 2000, J Exp Med 192: 1165-1174), and the like, phosphatases include AK2 protein (Kim H et al., 2014, Nat Commun 5: 3351). These targets for regulating the phosphorylation status of FADD are known and widely studied, and molecular design, chemical synthesis, and activity evaluation of substrate analogs of these enzymes are carried out by conventional molecular design methods, by adjusting the activity of the above enzymes, substances that function to regulate the phosphorylation status of FADD are readily available. Based on these concepts, as early as 2010, there existed high-throughput methods for screening for compounds for regulating FADD phosphorylation status. These methods have been proven to be reproducible on a large scale and are routine and feasible (Khan A P et al. Human, 2010, J Bio mol Screen 15(9): 1063-1070). Thus, for screening for substances that regulate the phosphorylation status of FADD, these techniques are fully feasible, regardless of the corresponding target protein/high throughput screening method, and can be readily mastered by those skilled in the art.

TECHNICAL SOLUTION

The object of the present invention is to provide a method for regulating cell lipolysis and fatty acid oxidative metabolism, which comprises expressing a Fas-related death domain protein phosphorylation gene, or screening for substances that increase Fas-related death domain protein phosphorylation by using the Fas-related death domain protein phosphorylation level as a basis. The shared purpose of the above methods is to increase the phosphorylation of Fas-related death domain proteins.

Further, a method for regulating cell lipolysis and fatty acid oxidative metabolism, characterized by increasing intracellular cAMP concentration, increasing phosphorylation degree and activity of hormone sensitive esterase HSL; regulating PPARα transcriptional activity and increasing the activity of enzymes involved in fatty acid β oxidation, including peroxidase acyl-CoA oxidase 1 (Acox1), trihydroxyacyl-CoA dehydrogenase (Ehhadh), very long chain acyl-CoA dehydrogenase (Acadvl), long face Acyl-CoA dehydrogenase (Acad1) and medium-chain acyl-CoA dehydrogenase (Acadm).

Further, a use of the method for regulating lipolysis and fatty acid oxidative metabolism in preparation of a medicament for treating a lipid metabolic disorder disease.

Further, a use of the above-mentioned method for regulating lipolysis and fatty acid oxidative metabolism in the preparation of a medicament for treating a lipid metabolism disease, which is used in combination with a conventional drug and technique for treating a lipid metabolism disorder.

Further, a pharmaceutical composition characterized by a method of regulating a lipolysis and fatty acid oxidative metabolism, a combination formulation using a pharmaceutically acceptable carrier or a excipient or a diluent.

Further, a use of the method for regulating lipolysis and fatty acid oxidative metabolism in preparation of a medicament for treating a lipid metabolic disorder disease.

In a first aspect of the invention, provided is a method for regulating lipolysis and fatty acid oxidative metabolism, characterized by achieving such regulation by regulating phosphorylation of a Fas-associated death domain protein.

The above method for regulating lipolysis and fatty acid oxidative metabolism not only can improve the level of phosphorylation of hormone-sensitive esterase HSL and its activity, and enhance the transcriptional activity of PPARα, it but also can increase the activity of an enzyme which is involved in the process of fatty acid β-oxidation.

In a second aspect of the invention, provided is a method for screening for a substance capable of increasing phosphorylation of a Fas-associated death domain protein, characterized by using change in the level of phosphorylation of a Fas-associated death domain protein as a basis to screen for a substance that increases the phosphorylation of Fas-related death domain protein, thereby regulating lipolysis and fatty acid oxidative metabolism.

The method for screening for a substance capable of increasing the phosphorylation of a Fas-associated death domain protein, which is characterized by designating regulating protein(s) which are known for regulating the phosphorylation of a Fas-associated death domain protein as a target site, designing, synthesizing, or screening by known methods to obtain substances which are capable of regulating the phosphorylation level of a Fas-associated death domain protein, wherein the screening is based on the changes of the phosphorylation level of the Fas-related death domain protein.

The substance capable of increasing the phosphorylation of Fas-related death domain protein includes macromolecular substances capable of increasing the phosphorylation level of Fas-related death domain protein, such as proteins, nucleic acids, polysaccharides, fatty acids, vitamins and nano molecules thereof. Also included are small molecules that increase the level of Fas-related death domain protein phosphorylation, such as natural products, chemically synthesized or chemically engineered products, small organic molecules, inorganic molecules, and the like.

In a third aspect of the invention, provided is a method of regulating lipolysis and fatty acid oxidative metabolism by introducing a gene that mimics the phosphorylation of a Fas-associated death domain protein.

The above gene for mimicking Fas-associated death domain protein phosphorylation is characterized by that it is a human Fas-associated death domain protein mutation gene in which its serine194 is mutated to aspartic acid or glutamic acid. The above gene, which mimics the phosphorylation of Fas-associated death domain proteins, can be used for gene therapy.

In a fourth aspect of the invention, provided is a use of the above-described method for regulating lipolysis and fatty acid oxidative metabolism in the manufacture of a medicament for the treatment of a lipid metabolic disorder. The use can be made by applying alone of the substance obtained by screening for increase of phosphorylation of a Fas-associated death domain protein, or the gene that mimics Fas-related death domain protein phosphorylation in the preparation of a lipid metabolism therapy medicament, or by applying such substance or gene in combine with an existing lipid metabolism medicament to form a composition, or by combining the above treatment with an existing chemical medicine treatment, a traditional Chinese medicine treatment, a biological treatment, a physical therapy, or the like in a lipid metabolism treatment.

In a fifth aspect of the invention, provided is a pharmaceutical composition comprising a pharmaceutically acceptable carrier or an excipient or a diluent, and an effective amount of the method for regulating lipolysis and fatty acid oxidative metabolism as described in claim 1.

In a sixth aspect of the invention, provided is a specific use of the above-described method for regulating lipolysis and fatty acid oxidative metabolism in the preparation of a medicament for treating a lipid metabolic disorder.

BRIEF DESCRIPTION OF THE DRAWINGS

In order to make the content of the present invention easier to understand, the present invention will be further described in detail based on the specific embodiments with reference to the accompanying figures, in which.

Significance analysis was performed by t-test, *P<0.05, **P<0.01.

FIG. 4. Effect of FADD phosphorylation on body weight and fat content in normal mice FIG. 4A. Left: Anatomical photographs of 10-week-old Normal mice as control and FADD phosphorylated mice fed with a standard diet; Right: Photographs of white adipose tissue and liver tissue of Normal mice as control and FADD phosphorylated mice.

Figure 4A:
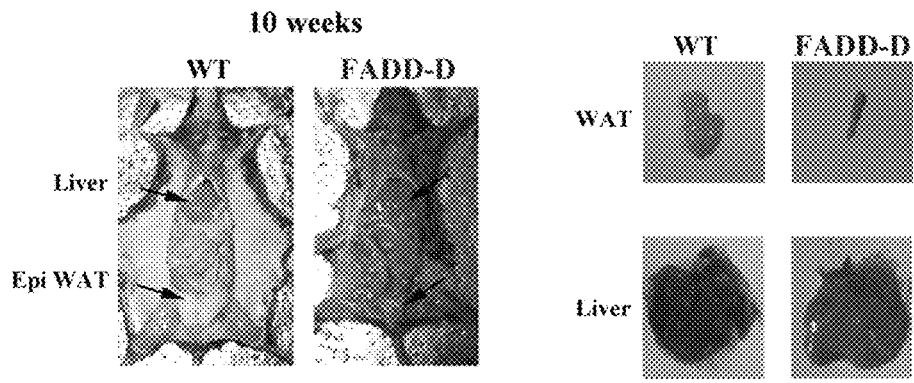
Figure 4B:
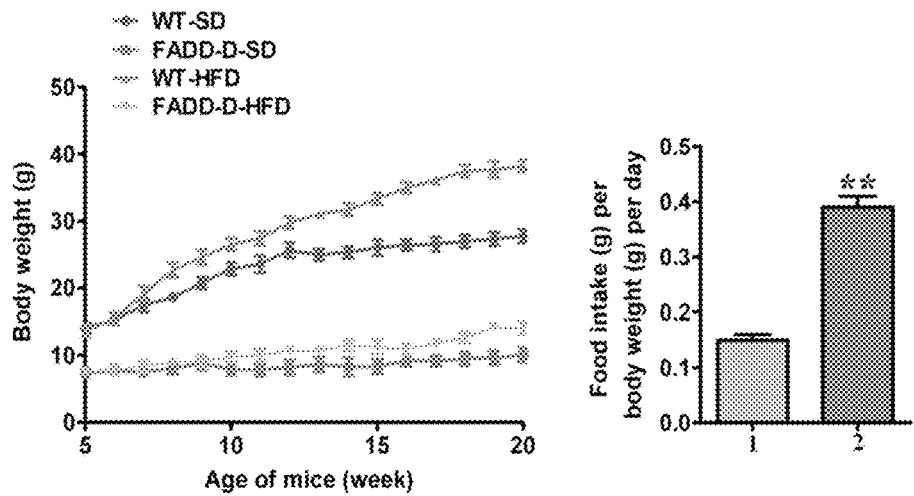

FIG. 4B. Left: Body weight growth curves of Normal mice as control fed with standard diet or high fat diet and FADD phosphorylated mice; Right: Per unit body weight daily intake of Normal mice as control and FADD phosphorylated mice: 1. Normal mice as control; 2. FADD phosphorylated mice.

Figure 4C:
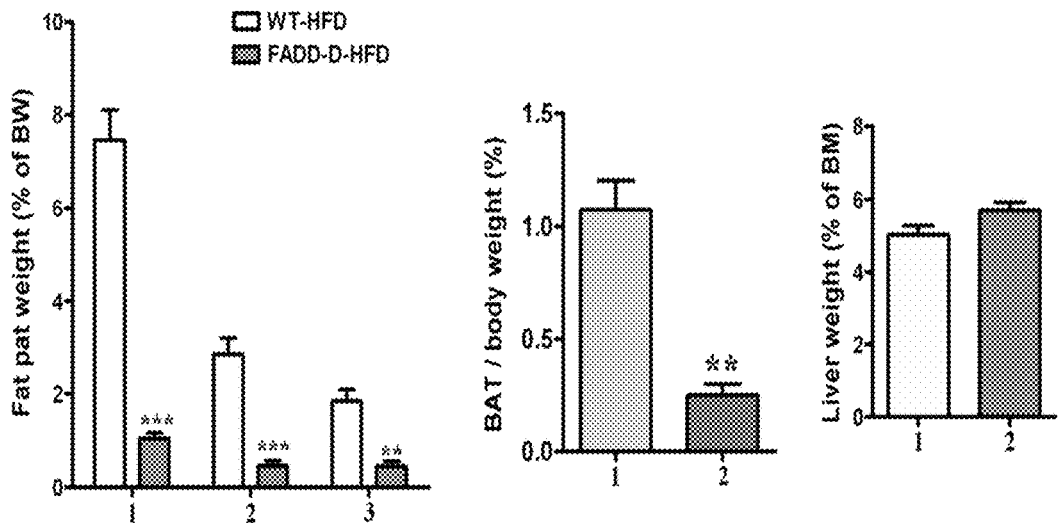

FIG. 4C. Left: The weight of each tissue fat mass as a percentage of body weight in Normal mice as control and FADD phosphorylated mice fed with a high-fat diet: 1.

Epididymis; 2. Kidney; 3. Inguinal. Meddle: The weight of the brown adipose tissue mass as a percentage of body weight in Normal mice as control and FADD-phosphorylated mice fed with a high-fat diet: 1. Normal mice as control; 2. FADD-phosphorylated mice. Right: Liver weight as a percentage of body weight in Normal mice as control and FADD-phosphorylated mice fed with a high-fat diet: 1. Normal mice as control; 2. FADD-phosphorylated mice.

Figure 4D:
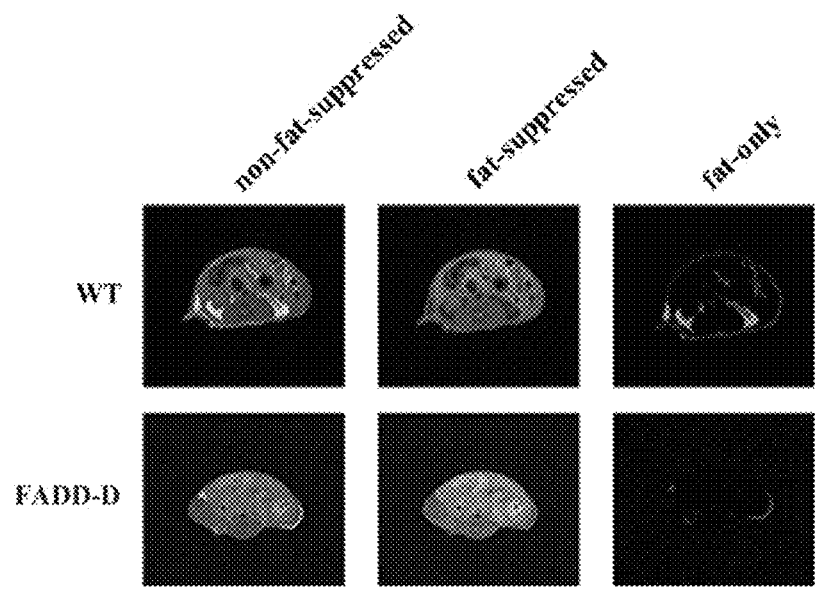

FIG. 4D. Distribution of fat in Normal mice as control and FADD-phosophorylated mice by nuclear magnetic resonance scanning.

Figure 4E:
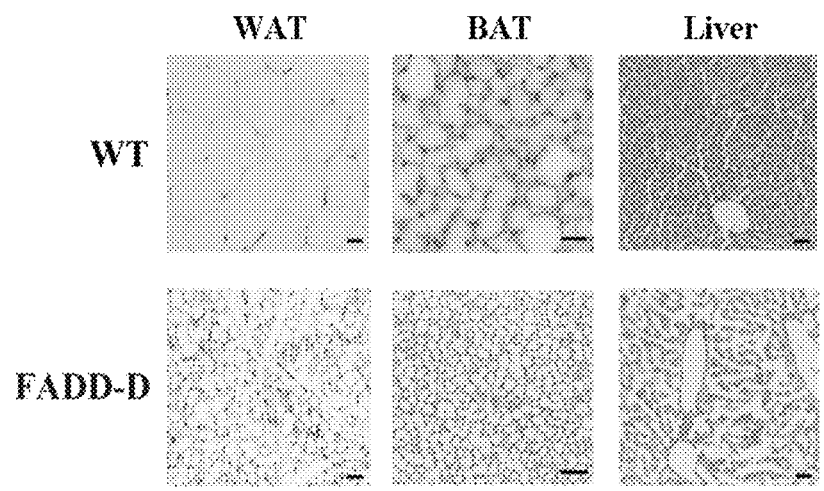

FIG. 4E. The white adipose tissue and brown adipose tissue of the mice were sectioned, and the sections were subjected to hematoxylin-eosin staining to observe the cell size and morphology of each tissue. The liver tissue was sectioned, and the sections were stained by oil red O staining to observe the content of triglyceride in the liver.

Significance analysis was performed by t-test, P<0.01, *P<0.001.

Figure 5A:
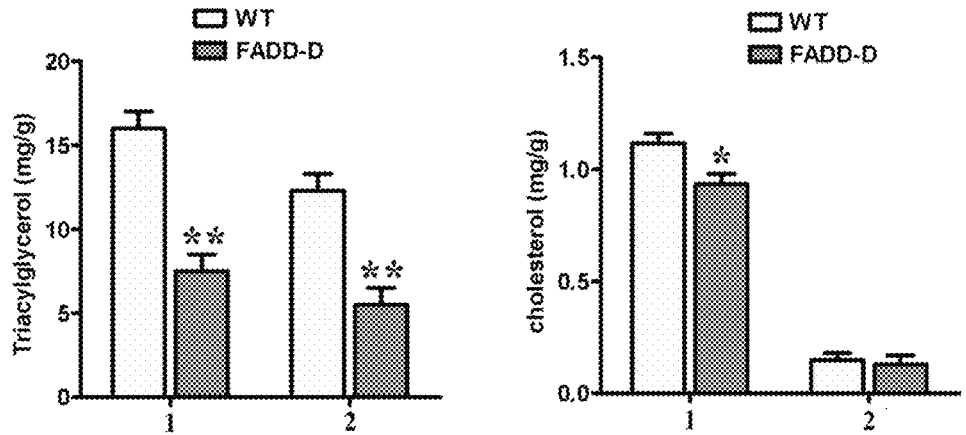

FIG. 5. Effects of FADD phosphorylation on various tissues and metabolic indicators such as serum triglycerides in mice FIG. 5A. Triglyceride content in liver and muscle of Normal mice as control and FADD phosphorylated mice fed with a high fat diet: 1. Liver; 2. Muscle.

Figure 5B:
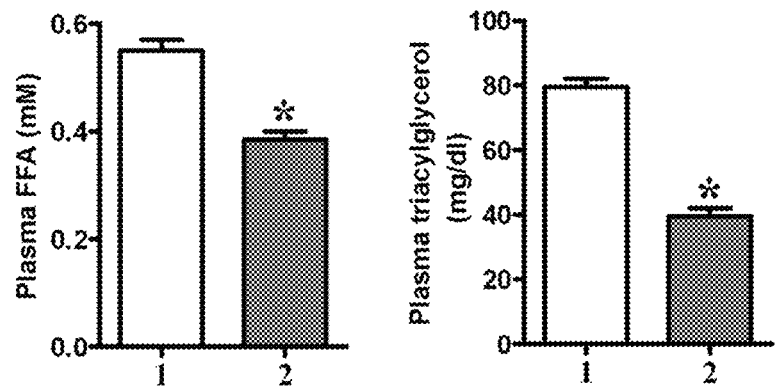

FIG. 5B. Content of free fatty acids and triglycerides in serum of Normal mice as control and FADD phosphorylated mice fed with a high fat diet: 1. Normal mice as control; 2. FADD phosphorylated mice.

Figure 5C:
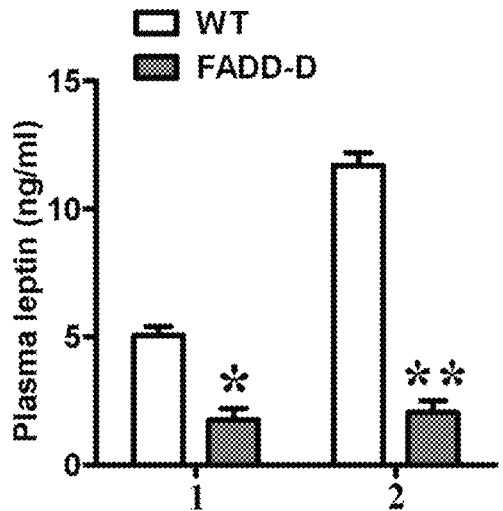

FIG. 5C. Serum leptin levels in Normal mice as control and FADD phosphorylated mice fed with a standard diet or a high fat diet: 1. Standard diet; 2. High-fat diet.

Significance analysis was performed by t-test, *P<0.05, **P<0.01.

Figure 6A:
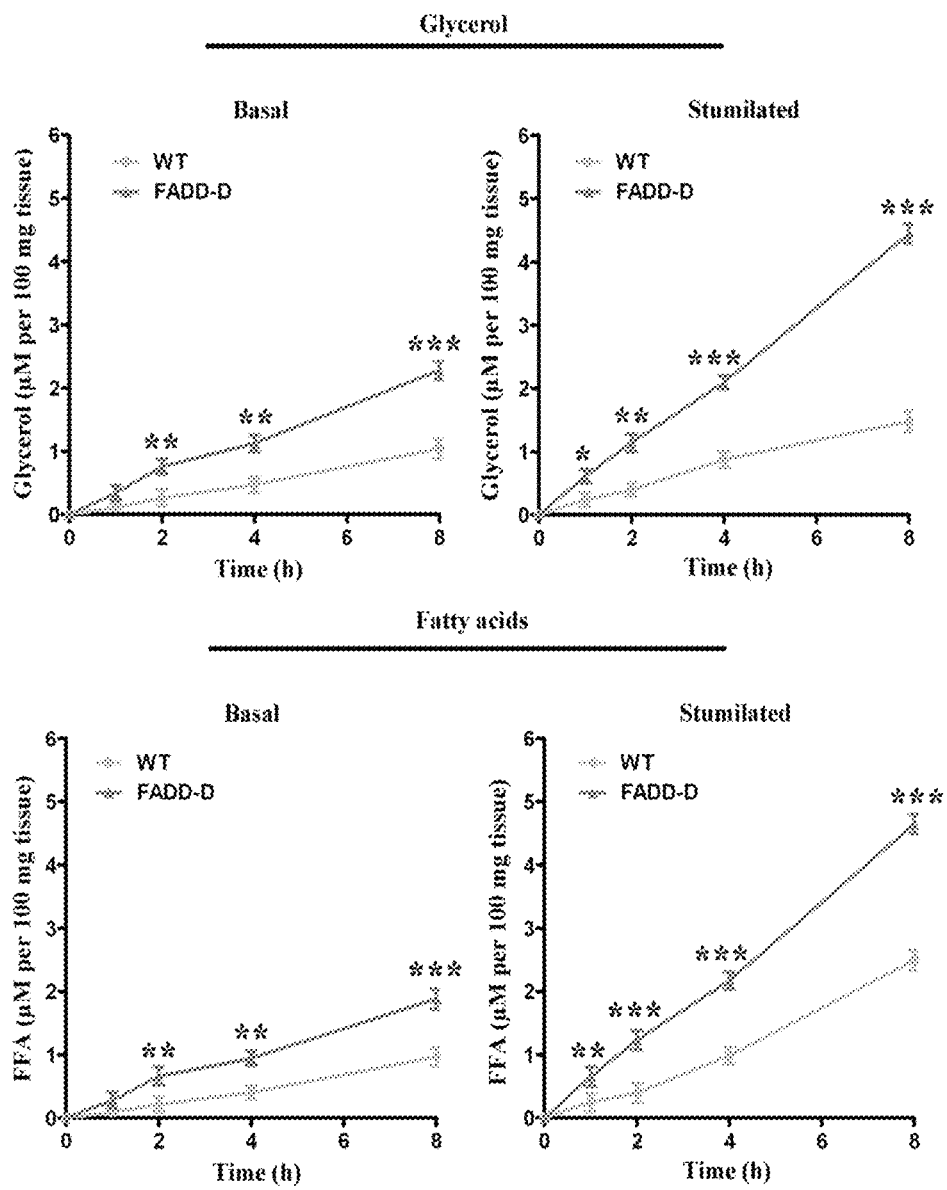

FIG. 6. Effect of FADD phosphorylation on the rate of lipolysis of triglycerides in mice FIG. 6A. Take the white adipose tissue mass of the epididymis of overnight fast mice, and measure the release amount of glycerol or free fatty acids every two hours under the stimulation of the basic conditions or isoproterenol, and plot the graph of lipolysis rate.

Figure 6B:
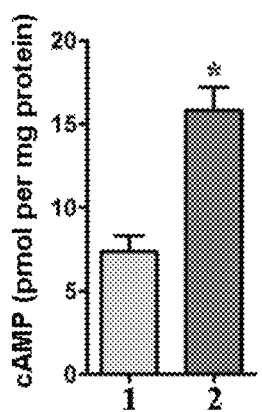

FIG. 6B. Content of cAMP in white adipose tissue of mouse epididymis fed by a high fat diet: 1. Normal mice as control; 2. FADD phosphorylated mice.

Figure 6C:
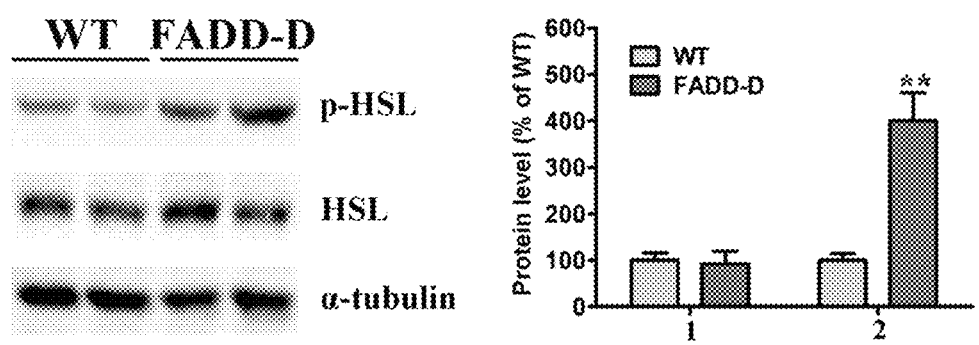

FIG. 6C. Western Blot was performed on the prepared white adipose tissue from the epididymis of mice fed with a high-fat diet to detect the protein expression levels of p-HSL, HSL and α-tubulin. The graph on the right shows the quantitative analysis of the results of Western Blot: 1. HSL; 2. p-HSLo.

Significance analysis was performed by t-test, *P<0.05, P<0.01, *P<0.001.

FIG. 7. Effect of FADD phosphorylation on the oxidation rate of fatty acids in mice FIG. 7A. White fat cells were isolated from the white adipose tissue of the epididymis of mice fed with a high-fat diet. The fatty acid oxidation rate of the fat cells was determined using a fatty acid β oxidation rate colorimetric assay kit: 1. Normal mice as control; FADD phosphorylated mice.

Figure 7A:
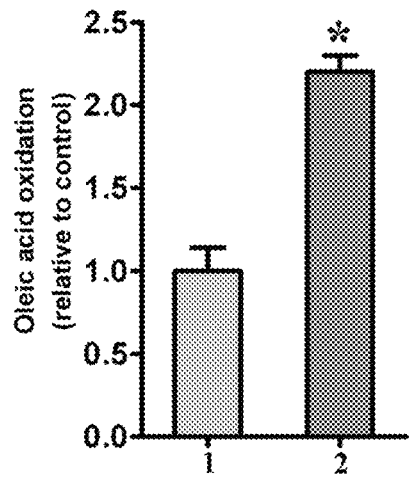
Figure 7B:
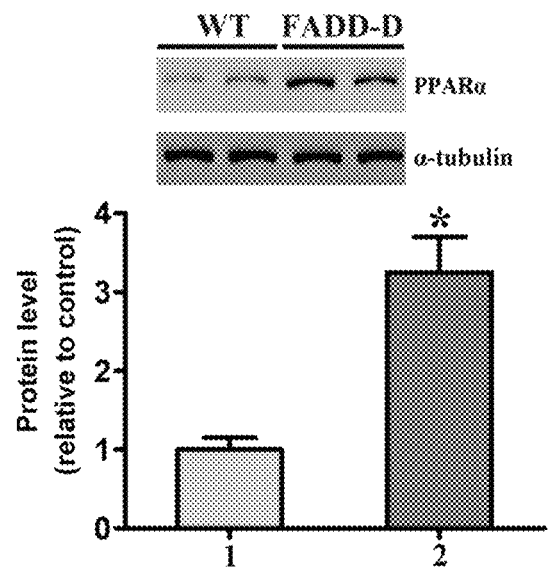

FIG. 7B. White adipose tissue of the epididymis of mice fed with a high-fat diet was made into a sample for Western Blot to detect the protein expression level of PPARα. The lower graph is a quantitative analysis of the results of Western Blot: 1. Normal mice as control; 2. FADD phosphorylated mice.

Figure 7C:
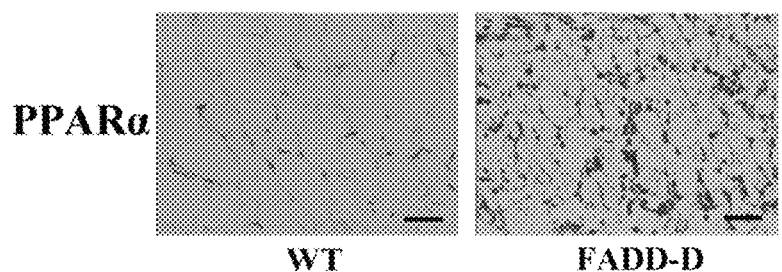

FIG. 7C. The white adipose tissue of the epididymis of the mice fed with a high-fat diet was sliced, embedded in paraffin, and immunohistochemically analyzed with antibodies against PPARα (4 mice per group), ruler=50 μm.

Figure 7D:
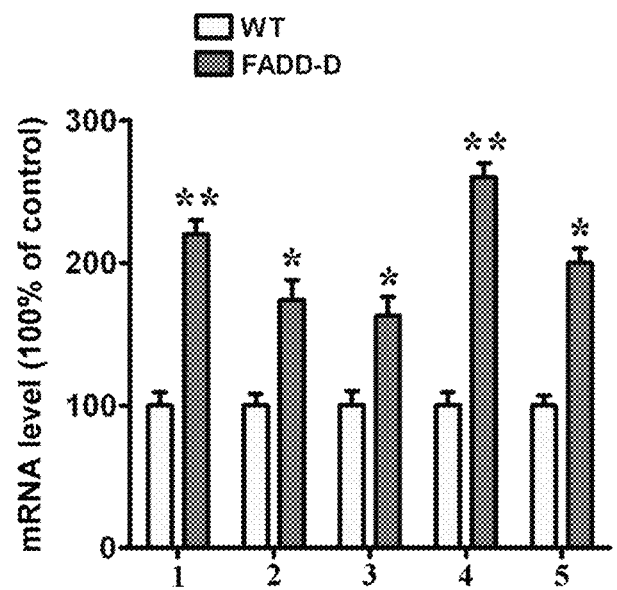

FIG. 7D. Detection of mRNA expression levels of lipid metabolism-related genes in white adipose tissue of epididymis of mice fed with a high-fat diet. 1. PPARα; 2. Acox1; 3. Ehhadh; 4. Acadm; wherein white is Normal mice as control, dark gray is FADD phosphorylated mice; 4-6 mice per group, three replicates per sample, with GAPDH as internal standard.

Figure 7E:
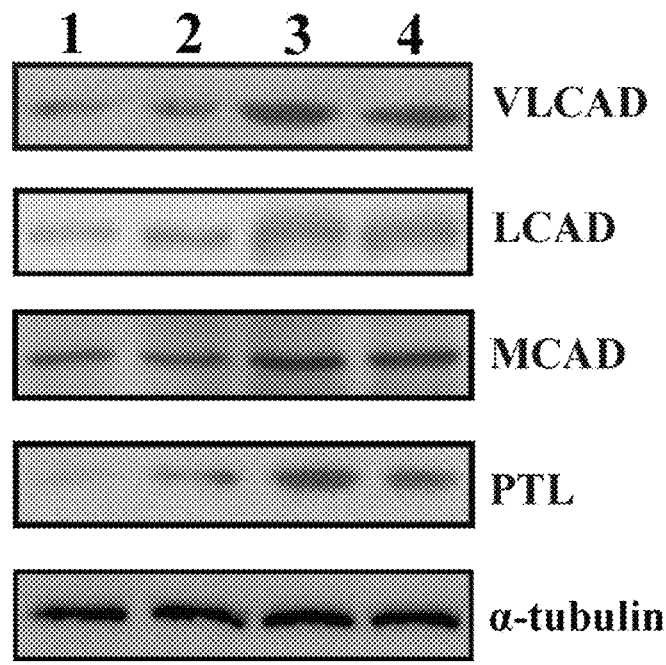

FIG. 7E. The white adipose tissue of the epididymis of mice fed with a high-fat diet was sampled for Western Blot to detect the expression levels of lipid metabolism-related proteins, including VLCAD, LCAD, MCAD and PTL, with α-tubulin as internal standard: 1. Normal mice as control; 2. ob/ob mice; 3. FADD phosphorylated mice; 4. FADD phosphorylated ob/ob mice.

Figure 7F:
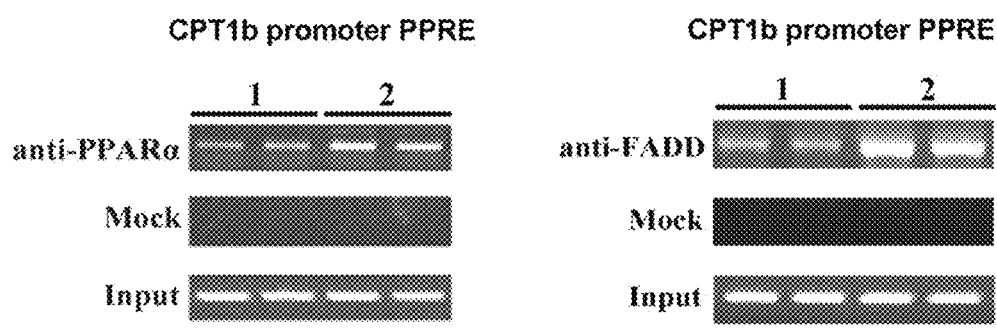

FIG. 7F. ChIP (chromatin immunoprecipitation) test of the white adipose tissue of the epididymis of the mice fed with a high-fat diet was performed for detecting the binding ability of PPARα (left) and FADD (right) to the PPRE (peroxisome proliferator-activated receptor response element) regulatory region: 1. Normal mice as control; 2. FADD phosphorylated mice.

Significance analysis was performed by t-test, *P<0.05, **P<0.01.

EXAMPLES OF THE INVENTION

Example 1

FADD Phosphorylation Up-Regulates the Rate of Fatty Acid Oxidative Metabolism in Mouse Embryonic Fibroblast Strains Mouse embryonic fibroblast cell lines in which FADD permanent phosphorylation (FADD-D, mutation of serine 191 to aspartic acid) and FADD permanent non-phosphorylation (FADD-A, mutation of 191 serine to alanine) was constructed. The cells were cultured, and the fatty acid oxidative metabolism rate of FADD phosphorylated cell line, FADD non-phosphorylated cell line and wild type cell line was determined by fatty acid β oxidation rate colorimetric detection kit (Shanghai Baoman Biotechnology Co., Ltd.) and compared, and the shape and number of mitochondria in three cell lines was observed by electron microscopy.

Figure 1A:
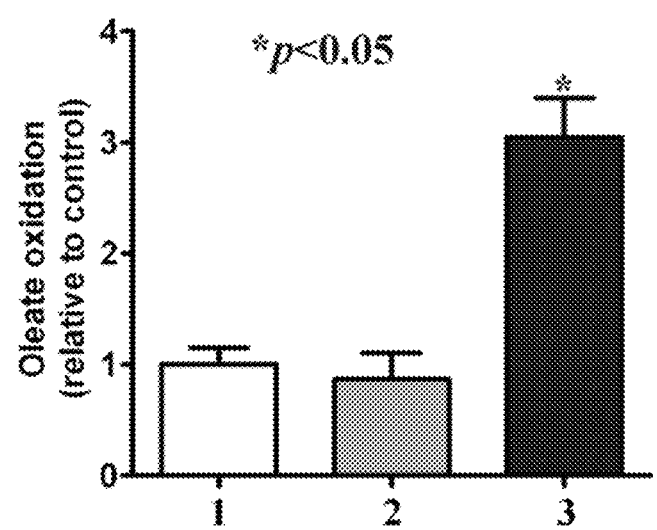
FIG. 1. FADD phosphorylation up-regulates the rate of fatty acid oxidative metabolism in mouse embryonic fibroblasts FIG. 1A. The rate of fatty acid oxidation in FADD phosphorylated cell lines is increased. Significance analysis was performed by t-test, *P<0.05.
FIG. 1B. The number of mitochondria in the FADD phosphorylated cell line is increased. Ruler=500 nm.
Figure 1B:
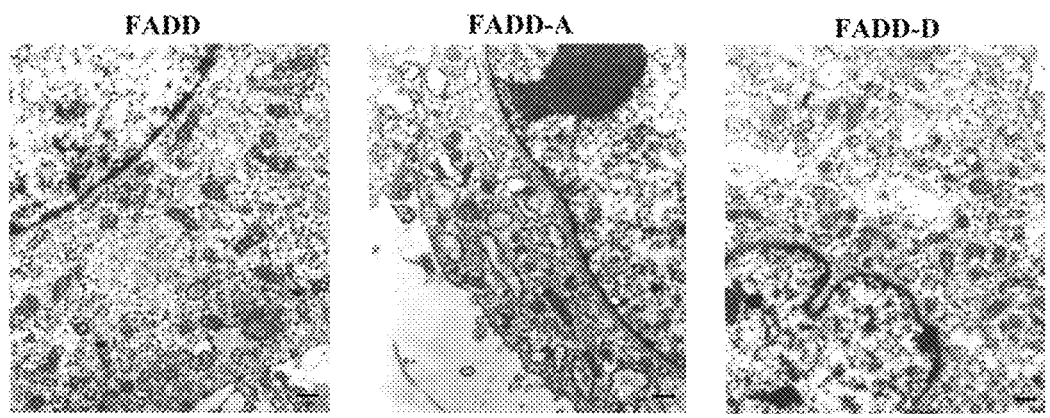

The oxidation rate of fatty acids showed that the oxidative metabolism rate of fatty acids in FADD phosphorylated cell lines was significantly higher than that in FADD non-phosphorylated cell lines and wild-type cell lines, while the fatty acid oxidative metabolism rate in FADD non-phosphorylated cell lines was not significantly different from wild-type cell lines (FIG. 1A). Mitochondria are the main sites of energy metabolism, and electron microscopy revealed that the number of mitochondria in FADD phosphorylated cell lines was also higher than that of FADD non-phosphorylated cell lines and wild-type cell lines (FIG. 1B), indicating that energy metabolism is more active in FADD phosphorylated cell lines.

Example 2

Comparison of FADD Phosphorylation Levels in Adipose Tissue Between Obese and Normal Human, ob/ob Obese and Normal Mice Human tissue sample preparation: White adipose tissue samples from normal and obese human were obtained from hospital surgery, and samples were used in Western Blot to analyze the level of FADD phosphorylation in the tissues.

Mouse tissue sample preparation: All experimental mice were housed in a ventilated, sterile, constant temperature and humidity SPF environment. Mice had free access to water and feed. Four ob/ob mice and four Normal mice as control were selected, and the mice were fed with a standard diet. When the mice were grown to the age of 20 weeks, the mice were sacrificed and dissected, and the white adipose tissue was taken out to prepare samples for Western Blot to analyze the level of FADS phosphorylation in its tissues.

Western Blot: The tissue was homogenized using cell lysate (50 mM Tris-HCl, pH 7.4, 250 mM NaCl, 50 mM NaF, 5 mM EDTA, 5 mM glycerol phosphate, 1 mM Na3VO4, 1% NP40), centrifuged at 12,000 rpm in a centrifuge, and the supernatant was collected, and the protein concentration was measured by the Bradford method. Equal amounts (about 50 μg) of the protein were separated by 12% SDS-PAGE gel electrophoresis, and then transferred to a PVDF membrane and finally tested with FADD antibodies.

FADD is present in a cell in two forms, a non-phosphorylated form and a phosphorylated form. Two bands can be detected with the FADD antibody, with the upper one being the phosphorylated form of FADD and the lower one being the non-phosphorylated form of FADD [Hua Z C et al., 2003, Immunity 18: 513-521]. Western Blot results show that the phosphorylated FADD band in obese human white adipose tissue was weaker than normal human (FIG. 2A); phosphorylated forms of FADD bands in white adipose tissue of 20-week-old ob/ob mice fed with a standard diet were significantly weaker than Normal mice served as control (FIG. 2B). These results indicate that a reduced expression level of phosphorylated form of FADD can result in obesity in mice or humans. That is, a phosphorylated form of FADD can cause mice or humans to become lean.

Example 3

Effect of Fas-Related Death Domain Protein (FADD) Phosphorylation on Body Weight and Body Fat Content in ob/ob Obese Mice All experimental mice were housed in a ventilated, sterile, constant temperature and humidity SPF environment. Mice had free access to water and feed. FADD-phosphorylated mice were mated with ob/ob mice as reported in the literature [Hua Z C et al., 2003, Immunity 18: 513-521] to obtain FADD-phosphorylated ob/ob mice, and genotypes were identified by PCR.

Six mice of each genotype were selected, and the mice were fed with a standard diet. The mice were weighed every week from the 6$^{th}$ week, and the mice were weighed until 35 weeks, and the body weight growth curves of the mice were drawn and a metabolic cage was used to calculate daily intake of the mice. The body shape and the size of the white adipose tissue of the epididymis and the liver of the 20-week-old ob/ob mice and FADD-phosphorylated ob/ob mice were compared. The weight of the white fat mass in the epididymis, kidney, and groin of the mouse was weighed and compared.

Figure 3A:
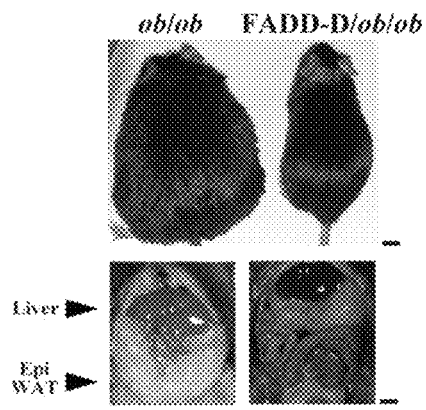
FIG. 3. Effect of FADD phosphorylation on body weight and fat content in ob/ob obese mice FIG. 3A. Upper: Photographs of 20-week-old ob/ob mice and FADD-phosphorylated ob/ob mice fed with a standard diet; Bottom: fat photographs of liver and epididymis of ob/ob mice and FADD phosphorylated ob/ob mice.
FIG. 3B. Left: Weight growth curves of ob/ob mice and FADD phosphorylated ob/ob mice fed with a standard diet; Right: Daily food intake of ob/ob mice fed with a standard diet and FADD phosphorylated ob/ob mice.
FIG. 3C. Weight of tissue fat mass in ob/ob mice and FADD phosphorylated ob/ob mice fed with a standard diet: 1. Epididymis; 2. Kidney; 3. Inguinal.
Figure 3B:
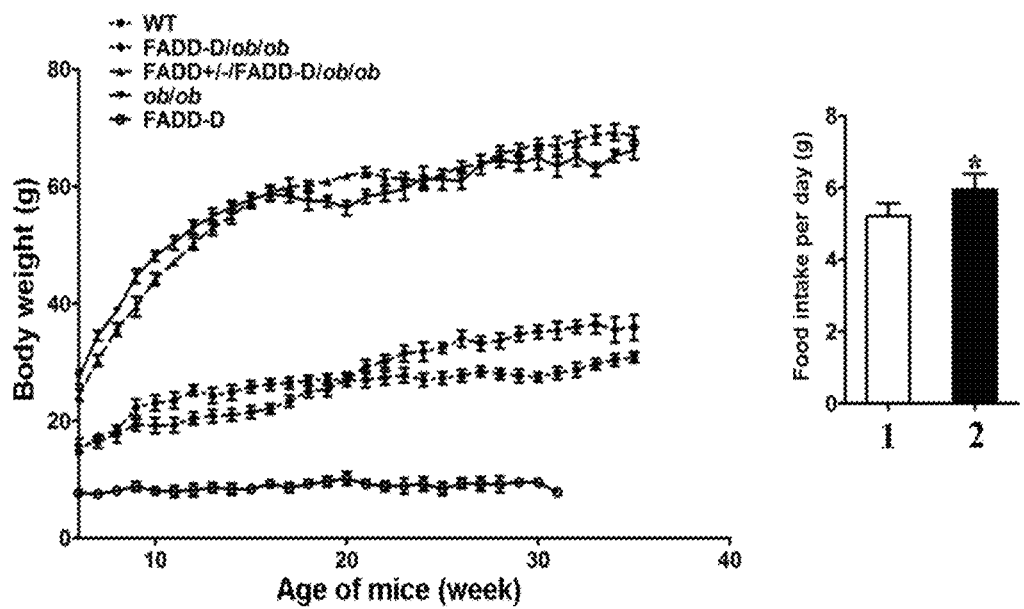

Since FADD is predominantly non-phosphorylated under normal conditions, the phosphorylated form is only present under specific physiological and pathological conditions. To observe the effect of FADD phosphorylation on lipid metabolism, in this patent a genetically engineered mouse was constructed that mimics FADD phosphorylation (mutating the mouse FADD gene 191 serine to aspartic acid to mimic phosphorylated FADD, this model has been internationally recognized) [Hua Z C et al., 2003, Immunity 18: 513-521], and the mouse was mated with ob/ob mice to obtain FADD phosphorylated ob/ob mice. The 20-week-old FADD-phosphorylated ob/ob mice fed with a standard diet were significantly thinner than ob/ob mice; their content of white fat in the epididymis was significantly less than that of ob/ob mice. The liver size was similar, but ob/ob mice clearly has fatty liver, while the liver of FADD-phosphorylated ob/ob mice had no fatty liver (FIG. 3A). The body weight growth curves of FADD-phosphorylated ob/ob mice and ob/ob mice were compared, and it was found that FADD-phosphorylated ob/ob mice grew significantly lower in weight than ob/ob mice and were similar to normal wild-type mice, that is, FADD phosphorylation can reverse the obese phenotype of ob/ob mice (FIG. 3B, left). Metabolic cage experiments found that although FADD phosphorylated ob/ob mice were much lower in body weight than ob/ob mice, the daily intakes were slightly higher than ob/ob mice, indicating that the decrease in body weight was not due to a decrease in food intake (FIG. 3B, right). In this patent the weight of white fat mass in three tissues of mice, including epididymis, kidney and groin was also measured.

Figure 3C:
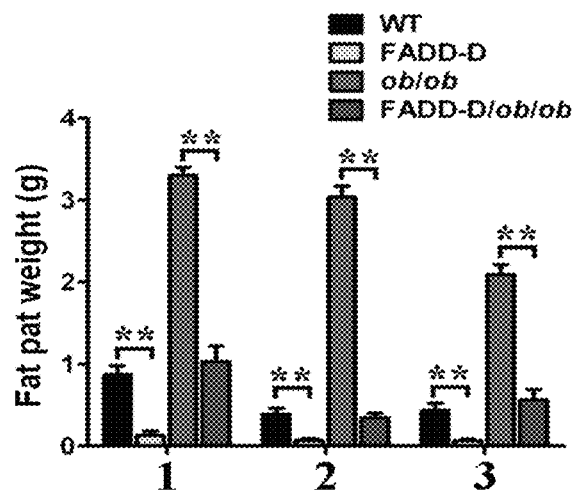

It was found that the weight of white fat mass in each tissue of FADD phosphorylated mice was also significantly lower than that of ob/ob mice (FIG. 3C), and this indicates that FADD phosphorylation can promote the decrease of body fat content in mice and cause the decrease of body weight in mice, which reverses the obese phenotype of ob/ob mice.

According to the results of this Example, in vivo expression of the protein which has "mutation of serine at position 194 of the FADD protein to aspartic acid" reversed the obese phenotype and achieved the purpose of treating obesity and obesity-related metabolic syndrome.

Worldwide, gene therapy is on the fast lane of development. The method of introducing a foreign gene into a host via a viral vector or a non-viral vector is well-established, and thus, it is convenient and economical to in vivo express a protein which has "mutation of serine at position 194 of the FADD protein to aspartic acid" in a gene therapy.

In addition, since FADD gene and protein are highly conserved among mammals, 68% of the amino acid residues of human and mouse FADD proteins are identical, with up to 80% homology in the primary structure of the protein. Similar functions of FADD in other mammals (including humans) have also been observed. (Chinnaiyan A M et al., 1995, Cell 81(4): 505-512; Boldin M P et al, 1995, J Biol Chem 270(14): 7795-7798.)

Figure 2A:
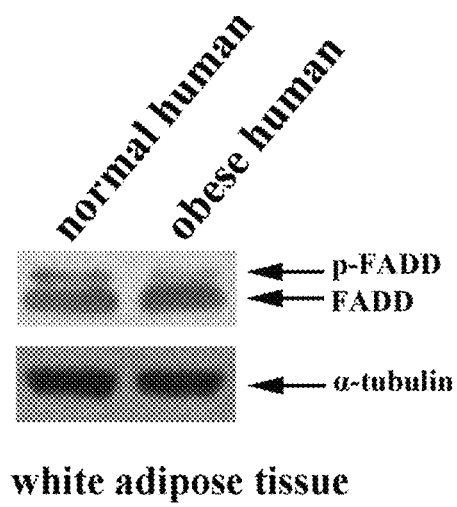
FIG. 2. Comparison of FADD phosphorylation levels in adipose tissue between obese and normal human, ob/ob obese and normal mice FIG. 2A. Western Blot was prepared by taking a white adipose tissue preparation from normal and obese human during surgery to detect FADD phosphorylation level.
FIG. 2B. White-fat tissue samples from 20-week-old ob/ob mice and normal control mice fed with a standard diet were prepared for Western Blot to detect FADD phosphorylation levels.
Figure 2B:
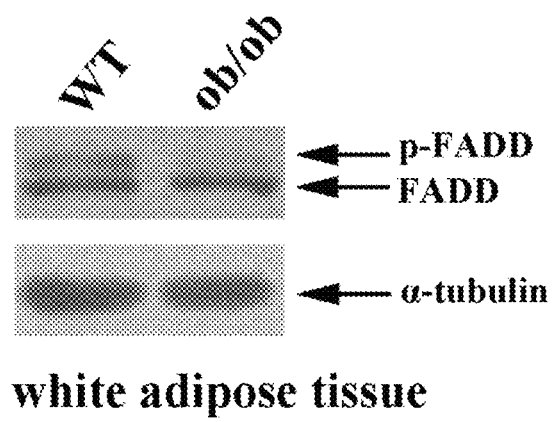

Moreover, from the results in Example 2 (FIGS. 2A and 2B), it can be seen that the band of the phosphorylated form of FADD in the obese human white adipose tissue was weaker than that of a normal person (FIG. 2A); The band of phosphorylated form of FADD in white adipose tissue of 20-week-old ob/ob mice fed with a standard diet were significantly weaker than normal control mice (FIG. 2B). These results indicate that a reduced expression level of phosphorylated form of FADD can cause obesity in mice or humans. That is, phosphorylated forms of FADD can render mice or human leaner.

Therefore, in view of the results shown in the present example, it is confirmed that the method of up-regulating FADD phosphorylation and thus achieving the downward regulation of fat content and body weight in obese mice is equally applicable to other mammals, especially humans.

Example 4

Effect of FADD Phosphorylation on Body Weight and Body Fat Content of Normal Genotype Mice In addition to studying the effect of FADD phosphorylation on body weight of ob/ob mice, the present invention also examined the effect of FADD phosphorylation on body weight and body fat content in normal wild-type mice, FADD phosphorylated mice were obtained as reported in the reference [Hua Z C et al, 2003, Immunity 18:513-521]. The experimental mice were divided into two groups, with one group being normal, control mice in the same litter, and the other group being FADD phosphorylated mice, Genotype was identified by PCR method. The weaned mice were fed with a standard diet to a 10-week-old size, and the mice were dissected and photographed to compare the epididymal fat content and liver size of normal control mice and FADD-phosphorylated mice. In addition, 6 mice of each genotype were selected, and the mice were fed with either a standard diet or a high-fat diet. The mice were weighed weekly from the $5^{th}$ week till the $20^{th}$ week to plot mouse body weight growth curves. The metabolic daily cage was used to calculate the daily intake of the mice. The weight of white fat mass in the epididymis, kidney and groin of the 20-week-old mice fed with the high-fat diet and the ratio of brown fat to body weight were compared. The body fat distribution was scanned using a nuclear magnetic resonance apparatus (Broker Medical, Germany). The mouse white adipose tissue and brown adipose tissue were taken into 10% phosphate buffered formalin, embedded in paraffin, cut into 5 μm thick slices, and the white adipose tissue and brown adipose tissue sections were stained with hematoxylin-eosin staining (HE), and the size and morphology of each cell were observed under a microscope. The liver tissues of the mice were taken, the sections were quickly frozen, and the frozen sections were stained with oil red O to compare the content of triglyceride in the liver tissues.

Similar to Example 3, FADD phosphorylation also caused normal mice to be leaner. Comparing to normal mice, FADD phosphorylated mice showed a significant decrease in epididymal fat content (FIG. 4A), and body weight growth rate was also significantly lower than that of normal control mice (FIG. 4B, left); Metabolic cage experiments found that although FADD phosphorylated mice weighed much lower than normal control mice, the daily intake per unit weight was even higher than that of normal control mice, indicating that the decrease in body weight was not caused by a decrease in food intake (FIG. 4B, right). This patent also tested the weight of white fat mass in three tissues of mice, including epididymis, kidney and groin. It was found that the weight of white fat mass in each tissue of FADD phosphorylated mice was also significantly lower than that of normal control mice (FIG. 4C, left), the brown fat content also decreased significantly (FIG. 4C, middle), while the liver size did not change much (FIG. 4C, right). MRI scans showed that FADD-phosphorylated mice were significantly lower in both subcutaneous fat and visceral fat than that of normal control mice (FIG. 4D). HE staining of tissue sections showed that the white fat and brown fat cells of FADD phosphory fated mice were significantly smaller than normal control mice; Liver oil red O staining results also showed that the triglyceride content in the liver of FADD-phosphorylated mice was significantly lower than that of normal control mice (FIG. 4E). These results indicate that FADD phosphorylation can inhibit mouse obesity caused by a high-fat diet or aging.

The results of Example 3 and Example 4 demonstrate that FADD phosphorylation not only can make ob/ob obese mice lean, but also can inhibit obesity of normal genotype mice caused by a high-fat diet or aging. Therefore, it is possible to treat obesity and related metabolic syndrome by a method of screening for a substance that can increase FADD phosphorylation based on the change of the level of phosphorylation of FADD. These substances mainly include macromolecular substances that can increase the phosphorylation level of FADD protein, such as proteins, nucleic acids, polysaccharides, fatty acids, vitamins and nano-molecules, and also include small molecular substances that can increase the phosphorylation level of FADD, for example, natural products, chemically synthesized or chemically engineered products, small organic molecules, inorganic molecules, et al. In view of the results of Example 2, the above method is equally applicable to humans.

Example 5

Effect of FADD Phosphorylation on Metabolic Indexes such as Triglycerides in Mice Tissues and Serum FADD phosphorylated mice were obtained as reported in the reference [Hua Z C et al, 2003, Immunity 18:513-521]. The mice in the experiment were divided into two groups, with one group being normal control mice in the same litter, and the other group being FADD phosphorylated mice. Genotype was identified by PCR method. The mice were fed with a high fat diet. The triglyceride and cholesterol contents in muscle and liver were detected by triglyceride detection kit (Shanghai Yinggong Biotechnology Co., Ltd.) and cholesterol detection kit (Shanghai Biyou Biotechnology Co., Ltd.), respectively. Serum free fatty acid content and triglyceride content were tested by free fatty acid test kit and triglyceride test kit (all purchased from Sigma). Leptin levels in serum were detected by suspension chips (Bio-Rad Laboratories, Hercules, Calif., USA).

In order to further study the effect of FADD phosphorylation on lipid metabolism, the triglyceride content in liver and muscle tissue were measured, and it was found that the content of triglyceride in liver and muscle tissue of FADD phosphorylated mice was significantly lower than the normal control mice (FIG. 5A, left), the cholesterol content of the FADD-phosphorylated mice liver was slightly lower than that of the normal control mice, and the cholesterol content in the muscle was comparable (FIG. 5A, right). After fed with a high-fat diet, the serum levels of free fatty acids and triglycerides in FADD-phosphorylated mice were significantly lower than those in normal control mice (FIG. 5B), and the serum leptin content was also significantly lower than that in normal control mice (FIG. 5C). These results indicate that FADD phosphorylation promotes the decomposition of triglycerides. The concentration of free fatty acids in the serum of FADD phosphorylated mice was also decreased, indicating that FADD phosphorylation may also promote the oxidative metabolism of fatty acids.

Example 6

Effect of FADD Phosphorylation on the Rate of Lipolysis of Triglyceride in Mice

FADD phosphorylated mice were obtained as reported in the reference [Hua Z C et al, 2003, Immunity 18:513-521]. The experimental mice were divided into two groups, one group was normal control mice in the same litter, and the other group was FADD phosphorylated mice. Genotype was identified by PCR method.

Determination of lipolysis rate: Take mouse white fat mass, prepare tissue homogenate, use free fatty acid detection kit (Sigma) and glycerol detection kit (Beijing Hongyue Innovation Technology Co., Ltd.) at different time points (0 hours, 2 hours, 4 hours, 6 hours, 8 hours) to measure the fatty acid and glycerol concentrations in the basal state or stimulation conditions (with the addition of 100 nM isoproterenol), and then the rate of lipolysis was plotted.

cAMP content determination: cAMP content was determined by competitive immunoassay (R&D).

Western Blot: Western Blot assay method is shown in Example 2, and the antibodies were assayed with HSL and phospho-HSL antibodies, respectively. Image J grayscale scanning was performed on the Western Blot image and quantitative analysis was performed.

Data analysis: All the results were shown in the form of mean±SEM, Differential analysis between the two genotypes was performed using a two-tailed Student's t-test in Prism software (GraphPad, San Diego, Calif.). Data were considered statistically different when the P value was less than 0.05.

White adipose tissue is the main site of lipid metabolism. In order to investigate the metabolic effects of FADD phosphorylation on triglycerides, it was observed in the present invention the rate of lipolysis of mouse white adipose tissue. The rate of triglyceride decomposition in FADD-phosphorylated mouse white adipose tissue was significantly higher than that in normal control mice, both under basal conditions and under isoproterenol stimulation (FIG. 6A). cAMP is a key signaling molecule in the classical lipolysis signaling pathway. The present invention further detected cAMP content in white adipose tissue. The results show that the cAMP content in white adipose tissue of FADD phosphorylated mice was significantly higher than that of normal control mice (FIG. 6B). cAMP promotes phosphorylation of the downstream hormone-sensitive esterase HSL, and the phosphorylated HSL is activated to promote the decomposition of triglycerides. Therefore, this patent further observed whether the phosphorylation level of HSL is affected by FADD phosphorylation. The results showed that the phosphorylation level of HSL in white adipose tissue of FADD phosphorylated mice was significantly higher than that of normal control mice (FIG. 6C), indicating that HSL was activated and promoted the decomposition of triglycerides, which is consistent with the FADD phosphorylation we observed earlier that accelerates the decomposition of triglycerides. These results indicate that FADD phosphorylation increases cAMP content in white adipose tissue, activates the lipolysis signaling pathway, promotes the decomposition of triglycerides, and reduces the body fat content, resulting in lower body weight in mice, which is in line with the results we observed.

Example 7

Effect of FADD Phosphorylation on the Oxidation Rate of Fatty Acids in Mice

FADD phosphorylated mice were obtained as reported in the reference [Hua Z C et al, 2003, Immunity 18:513-521]. The experimental mice were divided into two groups, with one group being normal control mice in the same litter, and the other group being FADD phosphorylated mice. Genotype was identified by PCR method.

Fatty acid oxidation rate determination: mice were fed with a high-fat diet. Take mouse white adipose tissue, collagenase digestion tissue, isolate white fat cells, and use fatty acid β oxidation rate colorimetric detection kit (Shanghai Baoman Biotechnology Co., Ltd.) to measure the fatty acid oxidation rate of FADD phosphorylated mice and normal control mice.

Western Blot: The detection method was the same as in Example 2.

RNA extraction and quantitative real-time PCR: Tissues were treated with TRIzol reagent (Invitrogen, Carlsbad, Calif., USA), and RNA was extracted according to the attached instructions, and then cDNA was prepared by reverse transcription using a PrimeScript RT reagent Kit (Takara, Otsu, Shiga, Japan). Quantitative real-time PCR (qRT-PCR) was performed on ABI (Applied Biosystems, Foster City. Calif., USA). Primers were as follows: PPARα: forward primer: 5'-TCGCGGGAAAGACCAGCAACAA-3' (SEQ ID NO: 1); reverse primer: 5'-GCCAGGCCGATCTC-CACAGC-3' (SEQ ID NO: 2); Acox1: forward primer: 5-CGCCGCCACCTTCAATCCAGAG-3' (SEQ ID NO: 3); reverse primer: 5'-TCCAGGCCGGCATGAAGAAAC-3' (SEQ ID NO: 4); Ehhadh: forward primer: 5'-TCCCCCAC-TACCATCGCCACAG-3' (SEQ ID NO: 5); reverse primer: 5'-ACCAAATCGCCCAGCTTCACAGAG-3' (SEQ ID NO: 6); Acadvl: forward primer: 5'-CCCATGGGCTCCCT-GAAAAGAAGA-3' (SEQ ID NO: 7); reverse primer: 5'-GGCCGCCTCCGAGCAAAAGAT-3' (SEQ ID NO: 8); Acadm: forward primer: 5'-TCGCCCCG-GAATATGACAAAA-3' (SEQ ID NO: 9); reverse primer: 5'-AGAACGTGCCAACAAGAAATACCA-3' (SEQ ID NO: 10); GAPDH: forward primer: 5'-ACT-GAGGACCAGGTTGTC-3' (SEQ ID NO: 11); reverse primer: 5'-TGCTGTAGCCGTATTCATTG-3' (SEQ ID NO: 12). All results are the average of 3 experiments with GAPDH as an internal reference.

ChIP (chromatin immunoprecipitation) experiment: mice were fed with a high fat diet, white adipose tissue and collagenase digestion tissue of mice were taken, white fax cells were isolated and cultured in 10 cm culture dishes.

The First Day:

1. After discarding the culture solution, 3 ml of cold PBS was added along the wall, the culture dish was slowly rotated to thoroughly rinse the cells with PBS, then the PBS was poured off and sucked with a pipette.

2. 4 ml of 4% paraformaldehyde was added to each dish, mixed well to cover the dish, and was shaken on a shaker for 10 minutes to make it be fixed on the dish.

3. adding 1.25 M of Glycine solution in drops to the dish on the shaker, reaching 450 μl/dish, and continue to shake for 5 minutes.

4. All the liquid was poured off, and wash the dish twice with cold PBS, at least 3 ml each time, and the cells were scraped with 1 ml PBS. The cells were collected by centrifugation at 3000 rpm for 5 minutes. The cells was washed again with PBS and the supernatant was discarded.

5. 100 μl of Nuclei Lysis Buffer (PI 1:100) was added to each tube, the cells were disbursed by blowing and placed on ice for 10 minutes.

6. 900 μl of IP dilution Buffer (PI 1:100) was added to each tube, an ice-water mixture was prepared, and the ultrasound was started.

7. Centrifuged at 12000 rpm for 10 minutes at 4 degrees, and the supernatant was taken and added with antibody (PPARα antibody or FADD antibody) in an amount of at least 2 μg, and mixed overnight on a 4 degree vertical mixer.

The Second Day:

8. Protein G was blocked with fish sperm DNA and incubated for 2 hours at 4 degrees.

9. After the blocked protein G was added to the sample, incubation was continued for 2 hours on a 4-degree vertical mixer.

10. The protein G was collected by centrifugation at 5000 rpm for 1 minute. The supernatant of 400 was stored for each sample, and then used as a control, and the supernatant was temporarily retained at −20 degrees.

11. The remaining supernatant was discarded, and the protein G is washed sequentially using the following buffers. The washing sequence was as follows:
  A. Low Salt Immune Complex Wash Buffer, wash once
  B. High Salt Immune Complex Wash Buffer, wash once
  C. LiCl Immune Complex Wash Buffer, wash once
  D. TE buffer, wash twice.

12. Prepare fresh Elution Buffer (1% SDS, 0.1M NaHCO3)

13. 200 ml of Elution Buffer was added to each tube, and mixed at room temperature for 15 minutes by shaking using a vortex shaker, and after 15 minutes of elution, centrifugation at 5000 rpm for 1 minute, and the supernatant was collected by suction. Afterward, it was further eluted with 200 μl of Elution Buffer for 15 minutes, and the supernatant was again collected by centrifugation and after mixing the two supernatants together, a total of 400 μl of the eluted product was obtained.

14. At this point each sample had 400 microliters of the eluted supernatant, and the previously retained 400 microliters of the control supernatant, then the two samples were processed in parallel at the same time.

15. Each sample was added with 16 μl of 5 M NaCl, incubated for 4 hours in a 65-degree water bath, and then frozen at −20° C. for use.

The Third Day:

16. After the samples were defrosted, 8 μl of 0.5 M EDTA, 16 μl of 1 M Tris-HCl, pH 6.5 and 4 μl of 100× proteinase K were added to each sample and incubated for 1 hour in a 50 degree water bath.

17. 280 μl of saturated NaCl was added to each 400 μl of sample and 700 μl of chloroform, and mixed well.

18. After centrifuged at 10,000 rpm for 10 minutes at 4° C., the supernatant was carefully pipetted into a 1 ml centrifuge tube, 20 μg of fish sperm DNA was added as carrier DNA to each sample, mixed well, and started to extract the genome.

19. After adding 1.3 ml of absolute ethanol, and placed on ice for 10 minutes, a slightly white turbidity was observed.

20. After centrifugation at 12,000 rpm for 10 minutes at 4 degrees, the supernatant was carefully pipetted, and the precipitate was washed with 75% ethanol and dried.

21. After dissolving the precipitate with 20 μl of DDW, PCR was performed. PCR primer: CPT1b, 5′ CCTGTGCTGGTCCCCAACTCACAGC-3′ (SEQ ID NO: 13) and 5′ CTCCTGGTGACCTTTTCCCTACNIT-3′ (SEQ ID NO: 14) (279 bp).

Free fatty acids in serum are mainly derived from the decomposition of triglycerides stored in adipose tissue. Although the rate of lipolysis in FADD-phosphorylated mice was increased, the serum free fatty acid concentration was lower than that in normal control mice, so it is speculated that the fatty acid oxidation rate of FADD-phosphorylated mice has also increased. Consistent with the above speculation, it was found in this patent that the fatty acid oxidation rate of FADD-phosphorylated mouse white adipose tissue was significantly higher than that of normal control mice (FIG. 7A), which is consistent with the results that the free fatty acid content in the serum of FADD phosphorylated mice is lower than that in the normal control mice. PPARα plays an important role in the regulation of fatty acid metabolism and promotes cell's uptake, transport, activation and β oxidation of fatty acids. This invention also examined the expression of the transcription factor PPARα in adipose tissue. Western blot and immunohistochemistry experiments all showed that the expression of PPARα in FADD-phosphorylated mouse adipose tissue was much higher than that in normal control mice (FIGS. 7B and 7C). Increased expression of PPARα activates its regulated expression of target genes involved in fatty acid oxidative metabolism. Consistent with this observation, it was found in this patent that the expression of PPARα and mRNA expression of several key enzymes involved in fatty acid oxidative metabolism in the FADD phosphorylation mouse white adipose tissue have all increased, including peroxidase acyl-CoA 1 (Acox 1), III Hydroxyacyl-CoA dehydrogenase (Ehhadh), very long chain acyl-CoA dehydrogenase (Acadv1) and medium chain acyl-CoA dehydrogenase (Acadm) (FIG. 7D). Acadv1, Acadm, long-chain acyl-CoA dehydrogenase (Acad1), and peroxidase 3-ketoacyl-CoA thiolase (PTL) protein expression levels have also increased significantly (FIG. 7E). The high expression of these enzymes promotes the up-regulation of fatty acid oxidation rates. In order to further investigate the transcriptional activity of PPARα and the regulation of fatty acid oxidation rate, this patent also uses ChIP assay to detect the transcriptional regulation of PPARα to carnitine palmitoyl transferase 1b (CPT 1b), one of the important enzymes in the fatty acid metabolism pathway. It was found that FADD phosphorylation promoted the binding of PPARα to the PPRE element of the CPT1b gene regulatory region, enhanced the expression of CPT 1b gene, and promoted the oxidative metabolism of fatty acids (FIG. 7F).

Phosphorylation of FADD increases the concentration of cAMP in adipose tissues, activates the classical lipolysis pathway, enhances the phosphorylation level of HSL, and promotes the decomposition of triglycerides into free fatty acids and glycerol. Phosphorylation of FADD also enhances the transcriptional level of PPARα, thereby increases the expression of PPARα-regulated enzymes involved in fatty acid metabolism and promotes the oxidative metabolism of fatty acids. Thus, FADD phosphorylation provides a new drug target for the treatment of lipid metabolic diseases including obesity. By using the FADD phosphorylation level as a screening marker, substances that regulate FADD phosphorylation can be obtained, thereby finding a drug that regulates lipid metabolism.

It was achieved by this invention, by introducing a FADD mutant gene which mimics FADD phosphorylation, the regulation of the expression of the key transcription factors or enzymes, such as hormone sensitive esterase (HSL), peroxisome proliferator-activated receptor alpha (PPARα) and peroxidase acyl-C©A Enzyme 1 (Acox 1), trihydroxyacyl-CoA dehydrogenase (Ehhadh), very long chain acyl-CoA dehydrogenase (Acadv1), long-chain acyl-CoA dehydrogenase (Acad1) and medium-chain acyl-CoA Hydrogenase (Acadm), and it thus effectively regulates the pace of lipid metabolism. Therefore, a gene therapy created based on a FADD mutant gene that mimics FADD phosphorylation will be an effective way of regulating lipid metabolism diseases.

Therefore, the method of regulating lipolysis and fatty acid oxidation rate by FADD phosphorylation can be directly applied to the identifying, and making of therapeutic drugs for lipid metabolism diseases, and also to the treatment of such diseases. The method can also be used in combination with existing lipid metabolism treatment methods such as traditional chemical treatment, traditional Chinese medicine treatment, biological treatment and physical therapy, which produces enhanced therapeutic effects.

The invention claimed is:

1. A method for promoting downregulation of the fat content and the weight of an obese mammalian body, wherein the method is carried out by phosphorylating Fas-related death domain protein phosphorylation of said obese mammalian body, wherein the phosphorylating is carried out by mimicking the expression of a protein corresponding to a gene of phosphorylated Fas-associated death domain protein.

2. The method of claim 1, wherein the mimicking protein corresponding to a gene of phosphorylated Fas-associated death domain protein is a protein obtained by mutating the serine at position 191 or 194 of the wild-type Fas-associated death domain protein to aspartic acid or glutamic acid.

3. The method of claim 1, wherein the phosphorylating Fas-related death domain protein of said obese mammalian body is carried out by treating said obese mammalian body by using a substance capable of increasing the phosphorylation level of Fas-related death domain protein in said obese mammalian body.

4. The method of any one of claims 1, 2-3, wherein the mammalian body is a mouse or a human.

5. The method of any one of claims 1, 2-3, wherein the enzyme involved in the fatty acid β-oxidation process includes peroxidase acyl-CoA oxidase 1, trihydroxy acyl-CoA dehydrogenase, very long-chain acyl-CoA dehydrogenase, long-chain acyl-CoA dehydrogenase, and mid-chain acyl-CoA dehydrogenase.

6. The method of any one of claims 1, 2 and 3, wherein said method is used in combination with a method of promoting lipolysis and fatty acid oxidation metabolism by a chemotherapeutic agent, a method of promoting lipolysis and fatty acid oxidation metabolism by a Chinese medicine, a method of promoting lipolysis and fatty acid oxidation metabolism by a biological product, or a method of physically promoting lipolysis and fatty acid oxidation metabolism.

* * * * *

SEQUENCE LISTING

```
<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: PPAR-alpha foward primer sequence

<400> SEQUENCE: 1
tcgcgggaaa gaccagcaac aa                                              22

<210> SEQ ID NO 2
<211> LENGTH: 20
<212> TYPE: DNA
<213> ORGANISM: Artificial Sequence
<220> FEATURE:
<223> OTHER INFORMATION: PPAR-alpha reverse primer sequence

<400> SEQUENCE: 2
gccaggccga tctccacagc                                                 20

<210> SEQ ID NO 3
<211> LENGTH: 22
<212> TYPE: DNA
<213> ORGANISM: Artificial Sequence
<220> FEATURE:
<223> OTHER INFORMATION: Acox1 foward primer sequence

<400> SEQUENCE: 3
cgccgccacc ttcaatccag ag                                              22

<210> SEQ ID NO 4
<211> LENGTH: 21
<212> TYPE: DNA
<213> ORGANISM: Artificial Sequence
<220> FEATURE:
<223> OTHER INFORMATION: Acox1 reverse primer sequence

<400> SEQUENCE: 4
tccaggccgg catgaagaaa c                                               21

<210> SEQ ID NO 5
<211> LENGTH: 22
<212> TYPE: DNA
<213> ORGANISM: Artificial Sequence
<220> FEATURE:
<223> OTHER INFORMATION: Ehhadh foward primer sequence

<400> SEQUENCE: 5
tcccccacta ccatcgccac ag                                              22
```

<210> SEQ ID NO 6
<211> LENGTH: 24
<212> TYPE: DNA
<213> ORGANISM: Artificial Sequence
<220> FEATURE:
<223> OTHER INFORMATION: Ehhadh reverse primer sequence

<400> SEQUENCE: 6
accaaatcgc ccagcttcac agag                                          24

<210> SEQ ID NO 7
<211> LENGTH: 24
<212> TYPE: DNA
<213> ORGANISM: Artificial Sequence
<220> FEATURE:
<223> OTHER INFORMATION: Acadvl foward primer sequence

<400> SEQUENCE: 7
cccatgggct ccctgaaaag aaga                                          24

<210> SEQ ID NO 8
<211> LENGTH: 21
<212> TYPE: DNA
<213> ORGANISM: Artificial Sequence
<220> FEATURE:
<223> OTHER INFORMATION: Acadvl reverse primer sequence

<400> SEQUENCE: 8
ggccgcctcc gagcaaaaga t                                             21

<210> SEQ ID NO 9
<211> LENGTH: 21
<212> TYPE: DNA
<213> ORGANISM: Artificial Sequence
<220> FEATURE:
<223> OTHER INFORMATION: Acadm foward primer sequence

<400> SEQUENCE: 9
tcgccccgga atatgacaaa a                                             21

<210> SEQ ID NO 10
<211> LENGTH: 24
<212> TYPE: DNA
<213> ORGANISM: Artificial Sequence
<220> FEATURE:
<223> OTHER INFORMATION: Acadm reverse primer sequence

<400> SEQUENCE: 10
agaacgtgcc aacaagaaat acca                                          24

<210> SEQ ID NO 11
<211> LENGTH: 18
<212> TYPE: DNA
<213> ORGANISM: Artificial Sequence
<220> FEATURE:
<223> OTHER INFORMATION: GAPDH foward primer sequence

<400> SEQUENCE: 11
actgaggacc aggttgtc                                                 18

<210> SEQ ID NO 12
<211> LENGTH: 20
<212> TYPE: DNA
<213> ORGANISM: Artificial Sequence
<220> FEATURE:

```
<223> OTHER INFORMATION: GAPDH reverse primer sequence

<400> SEQUENCE: 12
tgctgtagcc gtattcattg                                              20

<210> SEQ ID NO 13
<211> LENGTH: 25
<212> TYPE: DNA
<213> ORGANISM: Artificial Sequence
<220> FEATURE:
<223> OTHER INFORMATION: PCT primer - CPT1b

<400> SEQUENCE: 13
cctgtgctgg tccccaactc acagc                                        25

<210> SEQ ID NO 14
<211> LENGTH: 25
<212> TYPE: DNA
<213> ORGANISM: Artificial Sequence
<220> FEATURE:
<223> OTHER INFORMATION: PCR primer - CPT1b

<400> SEQUENCE: 14
ctcctggtga ccttttccct acatt                                        25
```